United States Patent [19]
Ueno et al.

[11] 3,963,727
[45] June 15, 1976

[54] 1,2 DISUBSTITUTED BENZIMIDAZOLE DERIVATIVES

[75] Inventors: Katsujiro Ueno; Makoto Sato; Masahiro Arimoto; Hiroshi Kojima; Terukiyo Yamasaki; Takeo Sakurai, all of Tokyo, Japan

[73] Assignee: Daiichi Seiyaku Co., Ltd., Tokyo, Japan

[22] Filed: June 6, 1975

[21] Appl. No.: 584,347

[52] U.S. Cl.......................... 260/293.6; 260/293.78; 424/267
[51] Int. Cl.²........................................ C07D 401/04
[58] Field of Search................................ 260/293.6

[56] References Cited
UNITED STATES PATENTS

| | | | |
|---|---|---|---|
| 3,161,645 | 12/1964 | Janssen | 260/293.4 |
| 3,318,900 | 5/1967 | Janssen | 260/294 |

*Primary Examiner*—G. Thomas Todd
*Attorney, Agent, or Firm*—Oblon, Fisher, Spivak, McClelland & Maier

[57] ABSTRACT

A compound having the formula:

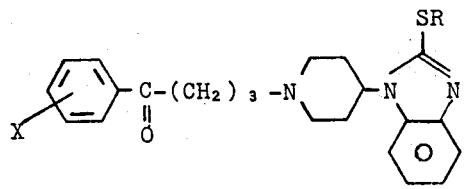

wherein R represents a hydrogen atom or a lower alkyl group, and X represents a halogen atom; or the acid-addition salt thereof having a distinctive neuroleptic activity.

3 Claims, No Drawings

1,2 DISUBSTITUTED BENZIMIDAZOLE DERIVATIVES

BACKGROUND OF THE INVENTION

1. Field of the Invention

The present invention relates to novel 1,2-disubstituted benzimidazole derivatives. More particularly, it relates to a novel compound represented by the following formula (I):

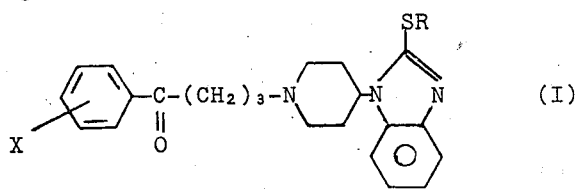

wherein R represents a hydrogen atom or a lower alkyl group, and X represents a halogen atom.

2. Description of the Prior Art

Up to now, compounds structually similar to those of this invention, benzimidazolinylpiperidines having the following chemical formula, are known and are described together with their depressive activity on central nervous system in Japanese Patent Nos. 2,062/1967.

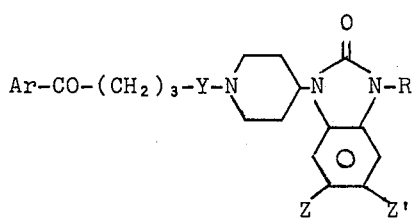

These known compounds, however, have not proved to be satisfactory for clinical use because of their undesirable side-effects or insufficient activities.

SUMMARY OF THE INVENTION

Accordingly, it is one object of this invention to provide novel compounds exhibiting stronger neuroleptic activities and less undesirable side-effects than those of known compounds.

The compounds of this invention can be prepared according to one of the alternative methods represented by the following reaction schematics (A) to (C):

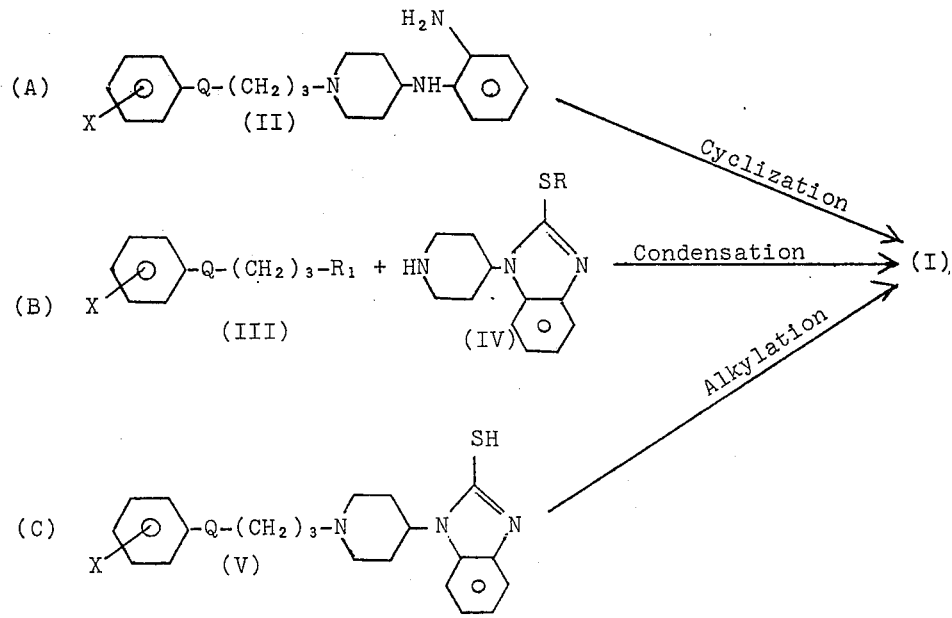

wherein R is as defined above, and Q represents a carbonyl or ethylene ketal group; $R_1$ represents a halogen atom such as chlorine, bromine, etc., or a reactive ester derivative of a hydroxy group such as a methane-sulfonyloxy group, a p-toluenesulfonyloxy group, etc.

DETAILED DESCRIPTION OF THE INVENTION

The compounds of this invention represented by the formula (I) can be prepared according to one of the above methods (A) to (C), the details of which are described below.

Method (A)

In this method, the desired compounds can be produced by reacting the raw materials (II), 2-aminoanilino piperidine derivative, with one of thio-compounds having a —CS— group such as carbon disulfide, potassium ethyl xanthate, thiourea, thiophosgen, ammonium thiocyanate, or ethyl xanthoformate, in the presence or absence a caustic alkali in a suitable solvent at a temperature between about 10° and about 100°C.

As the thio-compounds, carbon disulfide may be most preferably used. The raw materials (II) used in this method are novel and can be produced, for example, by reacting 4-(2-nitroanilino)piperidine with 2-(3-chloropropyl)-2-(4-fluorophenyl)-1,3-dioxorane and then reducing the resulting compound.

Method (B)

The compounds of this invention represented by the formula (I) can also be produced by reacting butanone derivatives (III) with piperidine derivatives (IV) at a temperature between about 50° and 170°C in a solvent, such as xylene, toluene, benzene, dioxane, dimethylformamide, butanol and the like, or without the solvents and, if necessary, by hydrolyzing the resulting product.

In this reaction, an acid-acceptor such as an alkali metal carbonate, an alkali metal bicarbonate, pyridine or triethylamine, and a reaction accelerator such as small amount of potassium iodide may also be used.

When butanone derivatives (III) in which Q is an ethylene ketal group is used, the resulting ketal compound is obtained in high yield and may be easily converted to the corresponding keto compound by hydrolyzing in an aqueous solvent.

Piperidine derivatives (IV) used in this method as starting materials are also novel and can be produced by reacting 1-(1-benzyl-4-piperidyl)-2-mercaptobenzimidazole with phenyl chloroformate and then hydrolyzing the resulting product.

Method (C)

When 2-alkylmercaptobenzimidazole derivatives are desired, the object compounds are prepared by alkylating the corresponding 2-mercaptobenzimidazole derivatives (V) with known alkylating agents such as dimethyl sulfate or an alkyl halide under the conventional reaction conditions.

The compounds of this invention represented by the formula (I) may be converted to their pharmaceutically useful or acceptable acid addition salts by reaction with an appropriate acid as, for example, an inorganic acid such as hydrochloric or sulfuric acid, an organic acid such as acetic, propionic or lactic acid.

The object compounds of the invention can be isolated using well known conventional techniques such as crystallization or extraction.

As is apparent from the above description, an appropriate method of preparation can suitably be employed.

It is appreciated that the most essential aspect of the present invention resides in the finding of highly, distinctive neuroleptc activities of certain novel 1,2-disubstituted benzimidazole derviatives and salts thereof.

The compounds of the invention have a characteristic substituent represented by —SR, wherein R is as defined above, on the 2-position of the benzimiazolyl nucleus. Therefore, the present compounds show excellent neuroleptic activities ordinarily not obtained by well known typical neuroleptic agents such as haloperidol, or analogous benzimidazoline derivatives shown hereinbefore, in which the most similar compound to the present invention compound is benperidol.

Particularly useful compounds of the present invention are those having the formula (I) wherein the aryl group

is a 4-fluorophenyl group, and R is a hydrogen atom or a methyl group. That is, 1-[1-(3-(4-fluorobenzoyl)-propyl)-4-piperidyl]-2-mercaptobenzimidazole (hereinafter referred to as Compound A) and 1-[1-(3-(4-fluorobenzoyl)propyl)-4-piperidyl]-2-methylmercaptobenzimidazole (hereinafter referred to as Compound B) are shown as representative compounds in the present invention.

The compounds of this invention have the marked neuroleptic-like properties such as anti-methamphetamine, antiapomorphine and deconditioning acitivities superior to those of known neuroleptics.

From the pharmacological standpoint, it is quite unique that the present compounds selectively exhibit main pharmaceutical effects at a certain effective administration dosage by which undesirable side-effects do not appear, while the known neuroleptics such as haloperidol or benperidol exhibit simultaneously both desired and undesired side-effects to almost the same extent at their effective dosages. So, it is impossible to expect selectively their desired main pharmaceutical effects. To demonstrate superiority of the present compounds on this point, the pharmacological properties of representative compounds of this invention were compared with those of haloperidol and benperidol which are known as typical antipsychotic drugs.

The pharmacological evaluation of the compounds has been made in rats on the basis of the comparison of their antagonism to methamphetamine taken as neuroleptic effect with an ability to induce catalepsy as a side-effect.

The compounds tested were administered as the form of a free base or acid salt. The experimental results are as follows.

(1) Anti-methamphetamine Test in Rats

Five male rats of Wistar strain weighing 130 to 210 g were used at each dosage level. Each group of five rats were separately kept individually in plastic cages. Test compounds were suspended in a 0.5% CMC aq. solution and administered orally in a volume of 2 ml/kg to the rats in the medication group, and only the solvent, in the corresponding volume, was given to the control group. One or 2 hours later, methamphetamine hydrochloride (10 mg/kg i.p.) were administered and then 1, 2 and 3 hours later, stereotyped behavior induced with methamphetamine hydrochloride was scored according to the following scoring system.

| Scoring System | |
|---|---|
| Score | Stereotyped behavior |
| 0 | Sleeping |
| 1 | Squatting |
| 2 | Looking about |
| 3 | Preening and Grooming |
| 4 | Ambulating |
| 5 | Rearing (more than 3 times) |
| 6 | Sniffing |
| 7 | Neck-Shaking |
| 8 | Licking, Biting and Gnawing |
| 9 | Body-Shaking, Walking Back and Rotating |
| 10 | Hard Ataxia and Death |

Comparing total score in the medicated group with that in control group, $ED_{50}$ and the confidence limits were calculated by the method of Litchfield-Wilcoxon (*J. Pharmacol*, 96, 99 (1949)). The results are shown in Table 1.

TABLE 1

| Test Compound | Time of Methamphetamine Injection after Treatment with Test Compd. (hr) | $ED_{50}$ and Its Confidence Limit (mg/kg, po) | Potency Ratio |
|---|---|---|---|
| Compound A | 2 | 0.054 (0.028 – 0.10) | 8.9 |
| Compound B | 1 | 0.17 (0.085 – 0.34) | 2.8 |
| Benperidol | 2 | 0.44 (0.20 – 0.97) | 1.1 |
| Haloperidol | 1 | 0.48 (0.18 – 1.2) | 1.0 |

(2) Catalepsy Test in Rats

Five male rats of Wistar strain weighing 130 to 210 g were used at each dosage level. After medication, both legs of the rats were put on a horizontal metal bar, 12 cm apart from the floor, and the rats were forced to stand on hind legs. Observation of rat behavior was made 1, 2, 4, 6, 8, 10, 12 and 24 hours later. When the animals showed this abnormal position for more than 60 seconds, cataleptic syndrome was regarded as positive. The results obtained are shown in Table 2 below.

TABLE 2

| Test Compound | Time after Medication (hr) | $ED_{50}$ and Its Confidence Limit (mg/kg, po)* | Potency Ratio |
|---|---|---|---|
| Compound A | 10 | 0.25 (0.14 – 0.46) | 3.5 |
| Compound B | 10 | 0.68 (0.37 – 1.3) | 1.3 |
| Benperidol | 8 | 0.92 (0.50 – 1.7) | 0.95 |
| Haloperidol | 8 | 0.88 (0.50 – 1.5) | 1.0 |

*These values were calculated from the responses at the time when maximum effect was observed.

From the results described above, the representative compounds of the present invention, Compound (A and (B), are highly effective in suppressing methamphetamine-induced stereotypy, while the compounds produce catalepsy only in higher doses. It has been confirmed that there exists a marked dissociation between the dose effective against methamphetamine and the dose inducing catalepsy in these compounds, while haloperidol and benperidol exhibit both the effects at almost the same dose level. Accordingly, the present compounds are evaluated to have a great advantage as an excellent neuroleptic drug in that they would have new modes of action not obtained in known butyrophenone type drugs.

Furthermore, the favorable pharmacological activities of the present compounds have been also recognized by the other methods. The details are shown hereinafter.

(3) Anti-apomorphine Test in Rats

Six male rats of Wistar strain weighing 120 to 200 g were used at each dosage level. Each group of six rats were separately kept individually in plastic cages and test compounds were administered orally about 30 minutes later. One, 2 or 4 hours later, apomorphine hydrochloride was administered (1.25 mg/kg i.v.) and then 20 minutes later, gnawing (stereotyped behavior induced by apomorphine) was observed for 1 minute. The effect against apomorphine was taken as positive when gnawing behavior was not noticed during the observation period of 1 minute. $ED_{50}$ was calculated from the dose inhibition percet relationship. The results are shown in Table 3.

TABLE 3

| Test Compound | $ED_{50}$ and Its Confidence Limit (mg/kg, po)* | Potency Ratio |
|---|---|---|
| Compound A | 0.095 (0.074 – 0.12) (2 hrs) | 7.5 |
| Compound B | 0.41 (0.26 – 0.64) (2 hrs) | 1.7 |
| Benperidol | 0.62 (0.38 – 1.0) (1 hr) | 1.1 |
| Haloperidol | 0.71 (0.52 – 0.97) (2 hrs) | 1.0 |

*These values were calculated from the responses at the time (figures in parentheses) when the maximum effect was observed.

(4) Conditioned Avoidance Test by Shuttle Box

Male rats of Wistar strain weighing 175°–215 g were used. Use was made of a shuttle box consisted of two chambers divided by a plate with a square hole. The floor of each chamber was made of steel-rod grid which can be charged electrically. The whole apparatus was maintained in a sound proof room. The training schedule was as follows. Each trial was initiated by supplying the sound of buzzer as conditioned stimulus for 3 seconds. Unless the rats escaped to another compartment 1.5 seconds thereafter, the grid floor was electrified for 4 seconds as unconditioned stimulus. Each rat was trained for more than 2 weeks with a daily session of 30 trials at an interval of 60 seconds. Drug studies carried out using the rats which showed more than a 80% avoidance rate.

Test compounds were suspended in a 0.5% CMC aq. solution and given orally in a volume of 2 ml/kg to the rats in the medication group and the solvent was given to the control group in the corresponding volume. Six rats per group were subjected to 10 consecutive trails 1, 2, 4, 6, 8 and 10 hours after medication, respectively. In this case, a 3-second interval was taken between the termination of the conditioned stimulus and the onset of the unconditioned one. $ED_{50}$ values at each time were calculated from the average percentages of avoidance failure.

The results are shown in Table 4.

TABLE 4

| Test Compound | $ED_{50}$ and Its Confidence Limit (mg/kg, po)* | Potency Ratio |
|---|---|---|
| Compound A | 0.06 (0.030 – 0.12) (6 hrs) | 8.8 |
| Compound B | 0.34 (0.18 – 0.65) (4 hrs) | 1.6 |
| Benperidol | 0.81 (0.44 – 1.5) (4 hrs) | 0.7 |
| Haloperidol | 0.53 (0.29 – 0.95) (4 hrs) | 1.0 |

*These values were calculated from the responses at the time (figures in parentheses) when the maximum effect was observed.

The present invention is further illustrated in greater detail by the following Preparation Examples (preparation of starting materials) and Examples, but they are given for illustrative purposes only and are not to be construed as limiting the invention.

PREPARATION EXAMPLE 1

A mixture of 7.34 g of 4-chloro-1-(4-fluorophenyl)-1-butanone ethylene ketal, 6.8 g of 4-(2-nitroanilino)-piperidine, 1.59 g of sodium carbonate, 0.1 g of potassium iodide and 10 ml of n-butanol was refluxed while stirring for 30 hours. After the reaction, the reaction solution was concentrated and subjected to alumina column chromatography. After the fraction eluted with benzene and a mixture of benzene and chloroform (1:1 by volume) was discarded, the fraction eluted with chloroform and a mixture of chloroform and ethanol (4:1 by volume) was collected and concentrated.

The residue was recrystallized from a mixture of diethyl ether and n-hexane to obtain 7.29 g of yellow needles of 1-[3-(4-fluorobenzoyl)propyl]-4-(2-nitroanilino)piperidine ethylene ketal having a melting point of 78° to 80.5°C.

Elemental Analysis for $C_{23}H_{28}FN_3O_4$: Calculated (%): C, 64.32; H, 6.57; N, 9.78. Found (%): C, 64.49; H, 6.66; N, 9.86.

A mixture of 4 g of the crystals, 100 ml of methanol and 4 ml of Raney nickel was stirred. After the absorption of hydrogen was completed, the catalyst was removed by filtration, and the solution was concentrated. The residue was recrystallized from diethyl ether to give needles of 1-[3-(4-fluorobenzoyl)-propyl]-4-(2-aminoanilino)piperidine ethylene ketal having a melting point of 113° to 113.5°C.

Elemental Analysis for $C_{23}H_{30}FN_3O_2$: Calculated (%): C, 69.14; H, 7.57; N, 10.52. Found (%): C, 69.18; H, 7.38; N, 10.44.

PREPARATION EXAMPLE 2

A mixture of 2.59 g of 1-(1-benzyl-4-piperidyl)-2-mercaptobenzimidazole, 3.76 g of phenyl chloroformate, 1.62 g of triethylamine and 150 ml of dried benzene was refluxed while stirring for 20 hours. After cooling, the solution was filtered and the filtrate was washed with water, dried, and concentrated. The residue was recrystallized from a mixture of chloroform and methanol to obtain colorless crystals of 1-(1-phenoxycarbonyl-4-piperidyl)-2-phenoxycarbonylmercaptobenzimidazole having a melting point of 200° to 203°C.

Elemental Analysis for $C_{26}H_{23}N_3O_4S$: Calculated (%): C, 65.94; H, 4.90; N, 8.87. Found (%): C, 65.99; H, 4.99; N, 9.02.

To 2.4 g of the crystals thus-obtained was added 70 ml of ethanol and 70 ml of a 10% sodium hydroxide solution. The mixture was refluxed for 5 hours and ethanol was distilled off from the solution. To the residue was added water and extracted with diethyl ether. The aqueous solution was acidified with acetic acid and extracted with diethyl ether. The aqueous solution was rendered alkaline with an aqueous ammonia and extracted with chloroform. The chloroform solution was dried and concentrated The residue was recrystallized from chloroform to obtain 1.03 g of colorless needles of 1-(4-piperidyl)-2-mercaptobenzimidazole having a melting point of 252° to 256°C.

Elemental Analysis for $C_{12}H_{15}N_3S$: Calculated (%): C, 61.77; H, 6.48; N, 18.01. Found (%): C, 61.74; H, 6.42; N, 17.73.

PREPARATION EXAMPLE 3

To a mixture of 5 g of 1-(1-benzyl-4-piperidyl)-2-mercaptobenzimidazole, 35 ml of methanol, 3.5 ml of water and 1.24 g of sodium hydroxide was dropwise added 2.11 g of dimethyl sulfate through 2.5 hours and continued stirring for an additional 0.5 hour. The reaction mixture was extracted with chloroform. The chloroform solution was dried and concentrated. The oily substance obtained was dissolved in diethyl ether and subjected to silica gel chromatography.

The fraction eluted with diethyl ether and chloroform was collected, and concentrated to obtain 6.77 g of a pale yellowish gummy substance. To the gummy substance was added a mixture of ethanol and hydrochloric acid to solidify the gummy substance. The product thus-obtained was collected and recrystallized from ethanol to obtain colorless crystals of 1-(1-benzyl-4-piperidyl)-2-methylmercaptobenzimidazole hydrochloride having a melting poing of 207° to 209°C.

Elemental Analysis for $C_{20}H_{23}N_3S \cdot HCl$: Calculated (%): C, 64.24; H, 6.47; N, 11.24. Found (%): C, 64.07; H, 6.29; N, 11.54.

4.55 g of the crystals thus-obtained was treated in the similar manner as employed in Preparation Example 1 to obtain 2.2 g of 1-(4-piperidyl)-2-methylmercaptobenzimidazole having a melting point of 114° to 115°C.

EXAMPLE 1

A mixture of 3.53 g of 4-chloro-1-(4-fluorophenyl)-1-butanone ethylene ketal, 6.4 g of 1-(4-piperidyl)-2-mercaptobenzimidazole as prepared in Preparation Example 1, 0.14 g of potassium iodide and 72 ml of normal butanol was heated at 130°C for 16 hours in a sealed tube. After cooling, benzene was added thereto and the resulting solution was filtered and evaporated. To the residue, 100 ml of ethanol and 100 ml of a 10% hydrochloric acid solution were added, refluxed for 1 hour, cooled, neutralized with a 10% sodium hydroxide solution, concentrated and extracted with 100 ml of chloroform three times.

The chloroform solution was subsequently washed with water, dried and concentrated to give a gummy substance. The gummy substance thus-obtained was dissolved in chloroform and subjected to silica gel chromatography and eluted successively with chloroform, a mixture of chloroform and ethanol (4:1 by volume), and a mixture of chloroform and ethanol (1:1 by volume). After removing the fraction eluted with chloroform, the fraction eluted with the chloroform-ethanol mixture was collected and the solvent was removed. The residue was recrystallized from acetone to give 1.82 g of colorless crystals of 1-[1-(3-(4-fluorobenzoyl)propyl)-4-piperidyl]-2-mercaptobenzimidazole having a melting point of 201° to 203°C.

Elemental Analysis for $C_{22}H_{24}FN_3OS$: Calculated (%): C, 66.47; H, 6.09; N, 1.57. Found (%): C, 66.30; H, 6.26; N, 10.65.

EXAMPLE 2

A mixture of 600 mg of 1-[3-(4-fluorobenzoyl)-propyl]-4-(2-aminoanilino)piperidine ethylene ketal as prepared in Preparation Example 1, 114 mg of potassium hydroxide, 154 mg of carbon disulfide, 20 ml of ethanol and 2 ml of water was heated at 80°C for 3 hours in a sealed tube. The reaction solution was concentrated and added thereto 10 ml of ethanol, 4 ml of water and 1 ml of a concentrated hydrochloric acid solution. Thereafter, the solution was neutralized with a sodium hydroxide solution and extracted with chloroform. The chloroform solution was washed with water, dried and concentrated. The residue was recrystallized from acetone to give 470 mg of colorless crystals of 1-[1-(3-(4-fluorobenzoyl)propyl)-4-piperidyl]-2-mercaptobenzimidazole having a melting point of 201° to 203°C.

EXAMPLE 3

A mixture of 0.99 g of 1-(4-piperidyl)-2-methylmercaptobenzimidazole as prepared in Preparation Example 3, 0.81 g of 4-chloro-1-(4-fluorophenyl)-1-butanone, 0.27 g of anhydrous sodium carbonate and 9 ml of normal butanol was stirred and refluxed for 56 hours. After the reaction, the solvent was distilled off and water was added to the residue, followed by extracting with chloroform. The chloroform solution was washed with water, dried and evaporated to give a gummy substance. The substance thus-obtained was dissolved in benzene and subjected to silica gel chromatography and eluted successively with 200 ml of a mixture of benzene and chloroform (1:2 by volume), 200 ml of a mixture of benzene and chloroform (1:1 by volume) and 300 ml of chloroform. After removing the fraction eluted with the mixture of benzene and chloroform (1:2 by volume), the fraction eluted with the mixture of benzene and chloroform (1:1 by volume) and chloroform was collectd, concentrated and recrystallized from a diethyl ether-normal hexane mixture to give 0.71 g of colorless crystals of 1-[1-(3-(4-fluorobenzoyl)propyl)-4-piperidyl]-2-methylmercaptobenzimidazole having a melting point of 98° to 98.5°C.

Elemental Analysis for $C_{23}H_{26}FN_3OS$: Calculated (%): C, 67.12; H, 6.37; N, 10.21. Found (%): C, 67.30; H, 6.37; N, 10.26.

EXAMPLE 4

A mixture of 400 mg of 1-[3-(4-fluorobenzoyl)-propyl]-4-(2-aminoanilino)piperidine ethylene ketal as prepared in Preparation Example 1, 112 mg of potassium hydroxide, 238 mg of carbon disulfide, 1 ml of ethanol and 0.2 ml of water was heated at about 80°C for 3 hours in a sealed tube. The mixture was concentrated and added thereto 10 ml of ethanol, 4 ml of water and 1 ml of concentrated hydrochloric acid. The solution was refluxed for 10 minutes. After cooling, the solution was neutralized with a sodium hydroxide solution and extracted with chloroform. The chloroform solution was washed with water, dried and concentrated. The residue was dissolved in chloroform and subjected to alumina column chromatography. The fraction eluted with chloroform was collected and concentrated. The residue was recrystallized from acetone to give 377 mg of colorless crystals of 1-[1-(3-(4-fluorobenzoyl)propyl)-4-piperidyl[-2-mercaptobenzimidazole having a melting point of 201° to 203° C.

EXAMPLE 5

A mixture of 398 mg of 1-[1-(3-(4-fluorobenzoyl)-propyl)-4-piperidyl]-2-mercaptobenzimidazole, 2 ml of isopropyl bromide and 5 ml of dioxane was heated for 38 hours at 120°C in a sealed tube. After cooling, the precipitate was separated by filtration and recrystallized from a chloroform-ethanol mixture to give 242 mg of colorless crystals of 1-[1-(3-(4-fluorobenzoyl)-propyl)-4-piperidyl]-2-isopropylthiobenzimidazole hydrobromide having a melting point of 222° to 224.5°C (decomp.).

Elemental Analysis for $C_{25}H_{30}FN_3OS \cdot HBr$: Calculated (%): C, 57.69; H, 6.00; N, 8.07. Found (%): C, 57.39; H, 6.08; N, 7.81.

EXAMPLE 6

15.9 g of 1-[1-(3-(4-fluorobenzoyl)propyl)-4-piperidyl]-2-mercaptobenzimidazole and 3.2 g of sodium hydroxide were dissolved in a mixture of 24 ml of water and 200 ml of methanol. To the solution, 7.06 g of dimethyl sulfate was added through 4 hours at room temperature (i.e., about 20°–30°C) and then the solution was stirred for an additional 20 minutes. After the reaction, the solution was concentrated and a diluted sodium hydroxide solution was added thereto, followed by extracting with chloroform. The chloroform solution was washed with water, dried and concentrated. The residue was recrystallized from ethanol to give colorless crystals of 1-[1-(3-(4-fluorobenzoyl)-propyl)-4-piperidyl]-2-methylmercaptobenzimidazole having a melting point of 98° to 98.5°C.

While the invention has been described in detail and with reference to specific embodiments thereof, it will be apparent to one skilled in the art that various changes and modifications can be made therein without departing from the spirit and scope thereof.

What is claimed is:

1. A compound having the formula:

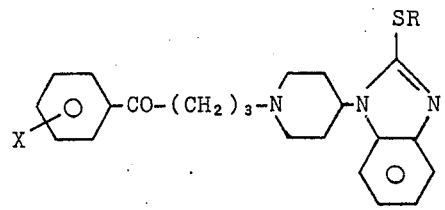

wherein R represents a hydrogen atom or a lower alkyl group and X represents a halogen atom; or the acid-addition salts thereof.

2. 1-[1-(3-(4-fluorobenzoyl)propyl)-4-piperidyl]-2-mercaptobenzimidazole and the acid-addition salts thereof.

3. 1-[1-(3-(4-fluorobenzoyl)propyl)-4-piperidyl]-2-methylmercaptobenzimidazole and the acid-addition salts thereof.

* * * * *